United States Patent
Green et al.

(10) Patent No.: US 9,636,220 B2
(45) Date of Patent: May 2, 2017

(54) AORTIC VALVE HOLDER WITH STENT PROTECTION AND/OR ABILITY TO DECREASE VALVE PROFILE

(71) Applicant: St. Jude Medical, Cardiology Division, Inc., St. Paul, MN (US)

(72) Inventors: Chad Joshua Green, Forest Lake, MN (US); James Michael Forsberg, Bloomington, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 0 days.

(21) Appl. No.: 14/989,448

(22) Filed: Jan. 6, 2016

(65) Prior Publication Data

US 2016/0113763 A1 Apr. 28, 2016

Related U.S. Application Data

(60) Continuation of application No. 14/683,354, filed on Apr. 10, 2015, now Pat. No. 9,259,316, which is a division of application No. 13/826,148, filed on Mar. 14, 2013, now abandoned.

(60) Provisional application No. 61/640,522, filed on Apr. 30, 2012.

(51) Int. Cl.
*A61F 2/24* (2006.01)

(52) U.S. Cl.
CPC .......... *A61F 2/2409* (2013.01); *A61F 2/2412* (2013.01); *A61F 2/2427* (2013.01); *A61F 2/2418* (2013.01)

(58) Field of Classification Search
CPC .... A61F 2/2409; A61F 2/2427; A61F 2/2439; A61F 2/243; A61F 2/2433; A61F 2/2424; A61F 2/2418; A61F 2/2403; A61M 39/06; A61B 17/3462; A61B 17/3498; A61B 2017/3464
USPC .................. 623/2.11, 1.18; 137/15.18, 15.19, 137/315.33, 844, 849
See application file for complete search history.

(56) References Cited

U.S. PATENT DOCUMENTS

| | | |
|---|---|---|
| 2,071,887 A | 2/1937 | Malin et al. |
| 3,630,512 A | 12/1971 | Paret |
| 4,399,856 A | 8/1983 | Anderson |
| 4,865,600 A | 9/1989 | Carpentier et al. |
| 5,476,510 A * | 12/1995 | Eberhardt ............. A61F 2/2427 606/1 |
| 5,716,401 A | 2/1998 | Eberhardt et al. |
| 6,065,744 A | 5/2000 | Lawrence |

(Continued)

FOREIGN PATENT DOCUMENTS

| | | |
|---|---|---|
| EP | 2387972 A1 | 11/2011 |
| WO | 2011/047137 A1 | 4/2011 |

OTHER PUBLICATIONS

International Search Report and Written Opinion for Application No. PCT/US2013/038737 dated Oct. 11, 2013.

*Primary Examiner* — Corrine McDermott
*Assistant Examiner* — Majid Jamialahmadi
(74) *Attorney, Agent, or Firm* — Lerner, David, Littenberg, Krumholz & Mentlik, LLP

(57) ABSTRACT

A valve holder is connectable to a prosthetic valve including a stent having a plurality of commissure posts. The valve includes a base, a plurality of legs extending from the base, and one of several mechanisms for deflecting the plurality of commissure posts radially inward so as to temporarily decrease the overall size of the prosthetic valve.

4 Claims, 13 Drawing Sheets

(56) References Cited

U.S. PATENT DOCUMENTS

| | | | |
|---|---|---|---|
| 6,214,043 B1 | 4/2001 | Krueger et al. | |
| 6,279,762 B1 | 8/2001 | Buchalter et al. | |
| 6,409,758 B2 | 6/2002 | Stobie et al. | |
| 7,503,929 B2 | 3/2009 | Johnson et al. | |
| 7,568,073 B2 | 7/2009 | Shen et al. | |
| RE42,395 E | 5/2011 | Wright et al. | |
| 8,273,118 B2 | 9/2012 | Bergin | |
| 2003/0125805 A1 | 7/2003 | Johnson et al. | |
| 2004/0024451 A1 | 2/2004 | Johnson et al. | |
| 2006/0220401 A1 | 10/2006 | Schwartz | |
| 2006/0241743 A1 | 10/2006 | Bergin et al. | |
| 2007/0203503 A1 | 8/2007 | Salahieh et al. | |
| 2008/0071367 A1 | 3/2008 | Bergin et al. | |
| 2009/0259305 A1 | 10/2009 | Lane et al. | |
| 2010/0004739 A1* | 1/2010 | Vesely | A61F 2/2427 623/2.11 |
| 2010/0121434 A1 | 5/2010 | Paul et al. | |
| 2010/0174363 A1 | 7/2010 | Castro | |
| 2011/0257736 A1 | 10/2011 | Marquez et al. | |
| 2012/0101569 A1 | 4/2012 | Mearns et al. | |

\* cited by examiner

_(12) United States Patent_
US 9,636,220 B2

AORTIC VALVE HOLDER WITH STENT PROTECTION AND/OR ABILITY TO DECREASE VALVE PROFILE

CROSS-REFERENCE TO RELATED APPLICATIONS

The present application is a continuation of U.S. patent application Ser. No. 14/683,354, filed Apr. 10, 2015, which is a divisional of U.S. patent application Ser. No. 13/826,148, filed Mar. 14, 2013, which claims the benefit of the filing date of U.S. Provisional Patent Application No. 61/640,522 filed Apr. 30, 2012, the disclosures of which are all hereby incorporated herein by reference.

BACKGROUND OF THE INVENTION

The current disclosure relates to prosthetic heart valves, and more particularly to apparatus for use in holding such valves prior to and during implantation of the valve in a patient.

Prosthetic heart valves are used for replacing diseased and/or deficient valves in a patient's heart. For example, a patient's mitral and/or aortic valves may need to be replaced by such prostheses. One illustrative type of prosthetic heart valve includes animal tissue that has been treated to make it suitable for long-term use in a patient's body. The valve implantation may be done in an "open heart" surgical procedure or a minimally invasive procedure.

During the implantation procedure, it may be desirable to temporarily modify the shape of the prosthetic tissue valve in certain respects in order to facilitate placement of the valve in the patient with good visualization and with good access for suturing the valve to the native tissue of the patient. For example, this temporary shape modification may include deflecting free end portions of the commissural posts of the prosthetic tissue valve radially inwardly. This shape modification is preferably done just prior to the implantation procedure to avoid any part of the valve taking an undesirable "set" during prolonged deformation, and may be especially useful in minimally invasive procedures in which there is limited space for a surgeon to work. Typical valve holders are disclosed, for example, in U.S. Pat. Nos. 4,865,600, 6,214,043, 6,409,758, 7,568,073, 7,503,929 and RE42,395.

The above aspects of prosthetic tissue valve handling may be aided by associating the valve with a so-called holder. This association may include, for example, a suture connection between the valve and the holder. The holder can be used to hold the valve in its storage liquid. When it is desired to use, or implant, the valve, a handle can be removably attached to the holder to remove the holder and valve from the storage liquid and to hold those components during the rinsing of the valve. Attachment of the handle to the holder (or subsequent manipulation of the handle relative to the holder) may also be used to cause the above-described temporary deformation of the valve. The handle may also be used to place the holder and valve in the patient. The handle may be removed from the holder during suturing of the valve into the patient. The handle may then be re-attached to the holder so that when the sutures connecting the valve to the holder are cut, the handle can be used to remove the holder from the patient, leaving only the valve in the patient.

Holders that are large, bulky, or that increase the effective diameter of the valve being held, may be undesirable. For example, if a surgeon is implanting a valve connected to a holder into a patient, a bulky holder may limit the ability for the surgeon to visualize the surgical working area. A surgeon may thus be provoked into removing the valve from a bulky holder during implantation. Without the protection of the holder, the valve may be more likely to be damaged during implantation.

From the foregoing it will be seen that a less bulky prosthetic valve holder that protects the valve and has the ability to decrease the valve profile is desired.

BRIEF SUMMARY OF THE INVENTION

In one embodiment of the invention, a holder is adapted for connection to a prosthetic valve in an assembled condition. The prosthetic valve may include a stent having a plurality of commissure posts. The holder may include a base. The holder may also include a plurality of legs extending in a direction from a first end connected to the base toward a free end, the direction including a component in an axial direction. The holder may further include a hub extending from the base in the axial direction, the hub having a plurality of pads extending radially outward and defining a circle having a hub diameter. The commissure posts of the stent may define a circle having a stent diameter, the stent diameter being greater than the hub diameter. In the assembled condition, each of the pads may be adapted to align with a respective one of the commissure posts. The base may include a shaft extending in the axial direction. The hub may include a bore defined by a wall of the hub, the bore being configured to slidingly mate with the shaft. The shaft may include a resilient tab and the wall of the hub may include an aperture configured to matingly receive the tab in an assembled relationship.

In another embodiment of the invention, a holder is adapted for connection to a prosthetic valve in an assembled condition. The prosthetic valve may include a stent having a plurality of commissure posts. The holder may include a base and a plurality of legs extending in a direction from a first end connected to the base toward a free end, the direction including a component in an axial direction. A ring holder may extend radially outward from each one of the plurality of legs. The holder may also include a wire ring having a central axis and a plurality of substantially straight sides joined by a plurality of connectors. The plurality of substantially straight sides may be spaced closer to the central axis than the plurality of connectors, the wire ring being mounted in the plurality of ring holders so as to surround the plurality of commissure posts and being rotatable about the central axis. The rotation of the wire ring may cause the substantially straight sides of the wire ring to contact the commissure posts and deflect the commissure posts radially inward. The prosthetic valve may have a constricted configuration and an unconstricted configuration, each of the plurality of connectors being positioned radially outward of a respective one of the commissure posts and the plurality of commissure posts defining a circle having an unconstricted diameter in the unconstricted configuration. Each of the plurality of substantially straight sides may be positioned radially outward of a respective one of the commissure posts and the plurality of commissure posts may define a circle having a constricted diameter in the constricted configuration. The constricted diameter may be smaller than the unconstricted diameter. The prosthetic valve may include three commissure posts, and the wire ring may be generally triangular with three connectors and three substantially straight sides.

In yet a further embodiment of the invention, a holder is adapted for connection to a prosthetic valve in an assembled condition. The prosthetic valve may include a stent having a plurality of commissure posts. The holder may include a base and a plurality of legs extending in a direction from a first end connected to the base toward a free end, the direction including a component in an axial direction. The holder may further include a finger pivotably coupled to each one of the plurality of legs. Each one of the fingers may be arcuate with a concave surface and a convex surface, the concave surface being adapted to contact one of the plurality of commissure posts. The convex surface of each one of the fingers may include a groove and at least one retaining element extending across the groove. A suture may extend between the groove and the at least one retaining element of each one of the fingers, the suture having a tensioned state and a relaxed state. Each one of the fingers may be positioned radially outward of a respective one of the commissure posts and the plurality of commissure posts define a circle having an unconstricted diameter in the relaxed state of the suture. Each one of the fingers may be positioned radially outward of a respective one of the commissure posts and the plurality of commissure posts may define a circle having a constricted diameter in the tensioned state of the suture. The constricted diameter may be smaller than the unconstricted diameter. A plurality of teeth may be associated with each one of the plurality of legs. A pawl may be included on each one of the fingers, the pawl being adapted to engage respective ones of the plurality of teeth to temporarily lock the finger in a fixed position relative to a respective one of the commissure posts. Each one of the fingers may be configured to move independently of the other ones of the fingers. Each one of the pawls may be configured to mate with successive ones of the plurality of teeth in an incremental fashion, such that as the pawl moves from one of the plurality of teeth to an adjacent one of the plurality of teeth, the concave surface of the finger applies increasing force to deflect the respective one of the commissure posts radially inward.

In a still further embodiment of the invention, a holder is adapted for connection to a prosthetic valve in an assembled condition. The prosthetic valve may include a stent having a plurality of commissure posts. The holder may include a base having a plurality of radially oriented bores and a plurality of legs extending in a direction from a first end connected to the base toward a free end. The direction may include a component in a first axial direction. The holder may further include a plurality of fingers extending radially outward from the base, each one of the fingers including a rod like portion slidably disposed in one of the radially oriented bores and a tip extending generally orthogonal to the rod like portion. Each one of the rod like portions may include a protrusion and the base may include a plurality of recesses arranged in multiple series, each series of recesses being associated with one of the radially oriented bores and being arranged in a linear array radially aligned with a respective one of the rod like portions. The protrusion of the rod like portion may be configured to mate with the plurality of recesses in the series. Each one of the fingers may movable from a first position in which the protrusion of the rod like member mates with a first one of the recesses in the series to a second position in which the protrusion of the rod like portion mates with a second one of the recesses in the series. Each one of the tips may be positioned radially outward of a respective one of the commissure posts and the plurality of commissure posts may define a circle having an unconstricted diameter when each one of the fingers is in the first position. The plurality of commissure posts may define a circle having a constricted diameter when each one of the fingers is in the second position. The constricted diameter may be smaller than the unconstricted diameter.

DETAILED DESCRIPTION

Figure 1:
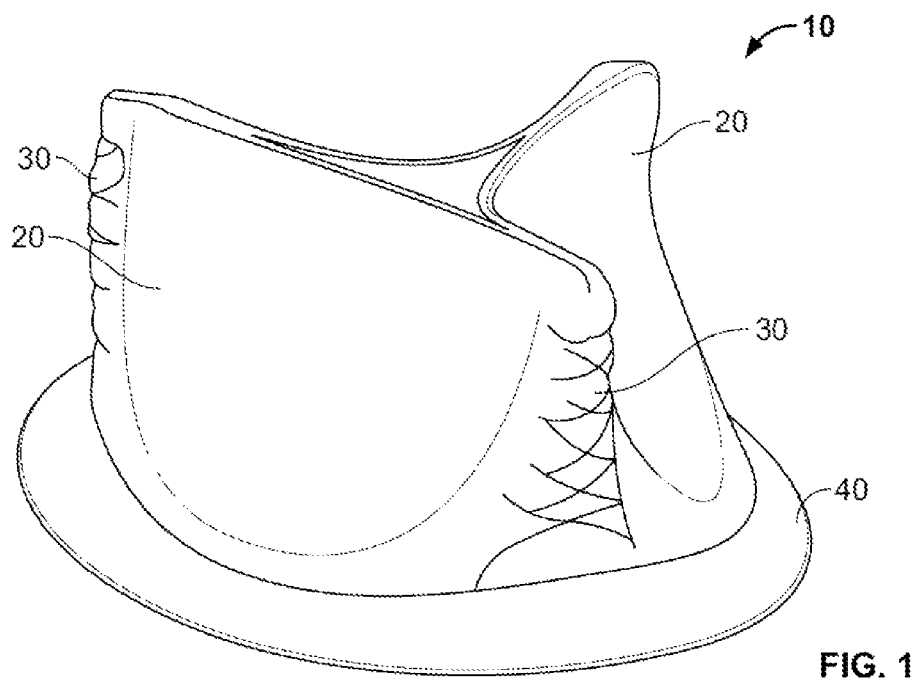
FIG. 1 is a top perspective view of a prosthetic heart valve according to the prior art.

FIG. 1 illustrates a typical prosthetic heart valve 10 according to the prior art to be used as a replacement for an excised native heart valve of a patient. The valve 10 includes a plurality of leaflets 20. Although a tricuspid valve is illustrated in FIG. 1, other configurations, such as bicuspid valves, may be used to replace a native heart valve. The leaflets 20 may be connected to a stent that provides structural support to the leaflets. For example, each leaflet 20 may be attached to commissure posts 30 extending generally axially from a base of the stent. In the valve 10 illustrated in FIG. 1, the leaflets 20 are positioned on an external portion of the stent. In other valves, the leaflets 20 may be positioned on an internal portion of the stent.

A suture ring or sewing cuff 40 may be attached to the stent and/or valve 10 at an inflow end of the valve. The cuff 40 is used to attach the valve 10 to the patient's heart tissue. The leaflets 20 may open at an outflow end to allow blood to flow through the valve in the antegrade direction, and coapt with one another to prevent blood from flowing back through the valve in the retrograde direction.

During implantation of the valve 10 into a patient's heart, sutures are generally passed through the sewing cuff 40 and heart tissue at the site of implantation while the valve is held approximately 6-8 inches above the heart. This positioning allows the surgeon working room and visibility for the procedure. Once the sutures are in place, the surgeon tightens the sutures to "parachute" the valve 10 into place and knots the sutures to fix the valve in its final position.

Figure 2:
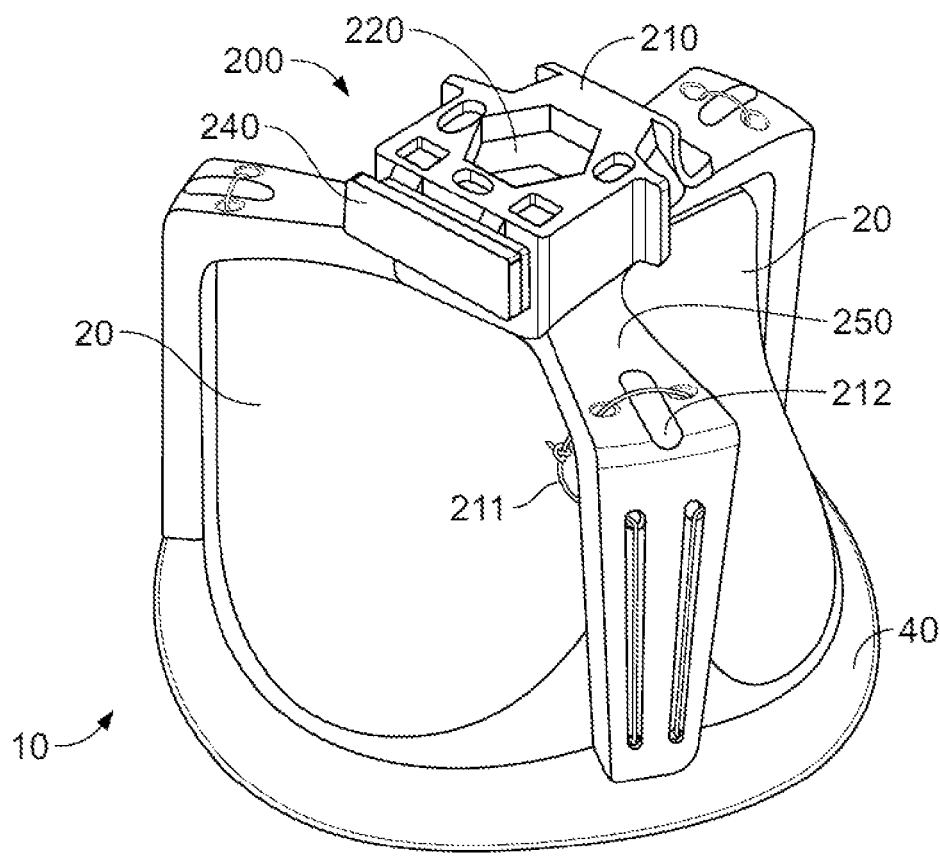
FIG. 2 is a top perspective view of a valve holder according to the prior art coupled to the valve of FIG. 1.
Figure 3:
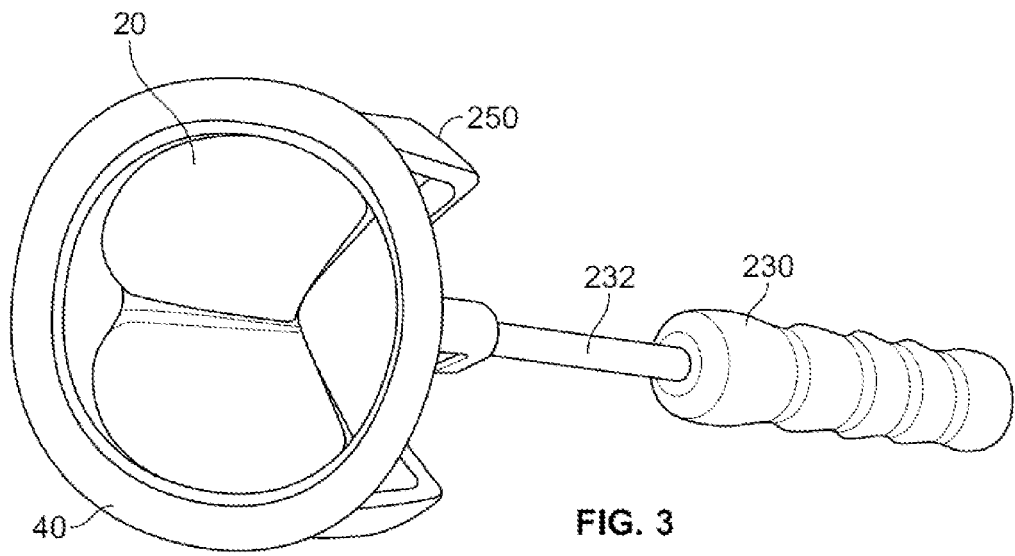
FIG. 3 is a bottom perspective view of a removable handle according to the prior art attached to the combination valve and valve holder of FIG. 2.

An embodiment of a valve holder 200 according to the prior art is illustrated in FIG. 2 attached to valve 10. Valve holder 200 generally includes a base 210 with an aperture 220 shaped to accept the shaft 232 of an elongated handle 230 (as seen in FIG. 3). The base may also include a locking mechanism 240 to lock the shaft 232 into base 210. Depressing the locking mechanism 240 releases the shaft 232 from the base 210 of the valve holder 200. Three fingers 250 extend radially outwardly from the base 210 and then downward generally parallel to a longitudinal axis of the valve 10. The fingers 250 are spaced from one another so as to correspond to the positions of commissure posts 30 of valve 10. Therefore, when the valve holder 200 is coupled to valve 10, fingers 250 will abut the commissure posts 30. The fingers 250 may be sutured to the valve 10 to fix the holder 200 in place relative to the valve. A suture 211 may pass through tracks in the finger 250, across the cuff 40, and further across a groove. The groove 212 allows a surgeon to easily cut the suture 211 when desired with a scalpel or other tool, by sliding the scalpel across the suture at the location of the groove.

After the handle 230 is attached to the holder 200, the surgeon may begin suturing the cuff 40 to the heart tissue as he or another person holds the valve 10 using the handle. Once the sutures are in place, the surgeon may use the handle 230 with the valve holder 200 to facilitate parachuting the valve 10 into its final position in the heart. When the valve 10 is near its final position, the surgeon may remove the handle 230 from the valve holder 200 and manually position the valve into its final position. The surgeon may confirm the position and knot the sutures to secure the valve 10 in this final position. Once the valve 10 is secure in its final position, the surgeon may cut the sutures fixing the valve 10 to the holder, and remove the holder (and the handle if still attached) from the patient. Although described with three fingers 250 for a tricuspid valve, it should be understood that the holder 200 may take on other configurations, such as a two finger configuration for supporting a bicuspid valve.

The valve holder 200 generally functions to protect part of the valve 10 or the entire valve and to provide structural support to the valve during the implant procedure.

It would be preferable if a valve holder could also facilitate deflection of the commissure posts 30 radially inward. Inward deflection of the commissure posts 30 makes the valve 10 somewhat smaller to give the surgeon a better view and more room in the surgical space, and may facilitate movement of the valve through the body into its final position in the heart. If the surgeon finds the holder too bulky, he may remove the holder during the suture tying and/or parachuting steps, leaving the valve 10 unprotected and more likely to be damaged during final insertion and positioning of the valve in the heart. It would be preferable to have a valve holder with a smaller effective diameter, as well as a valve holder that facilitates inward deflection of the commissure posts 30 to decrease the size of the valve during implantation.

Figure 4:
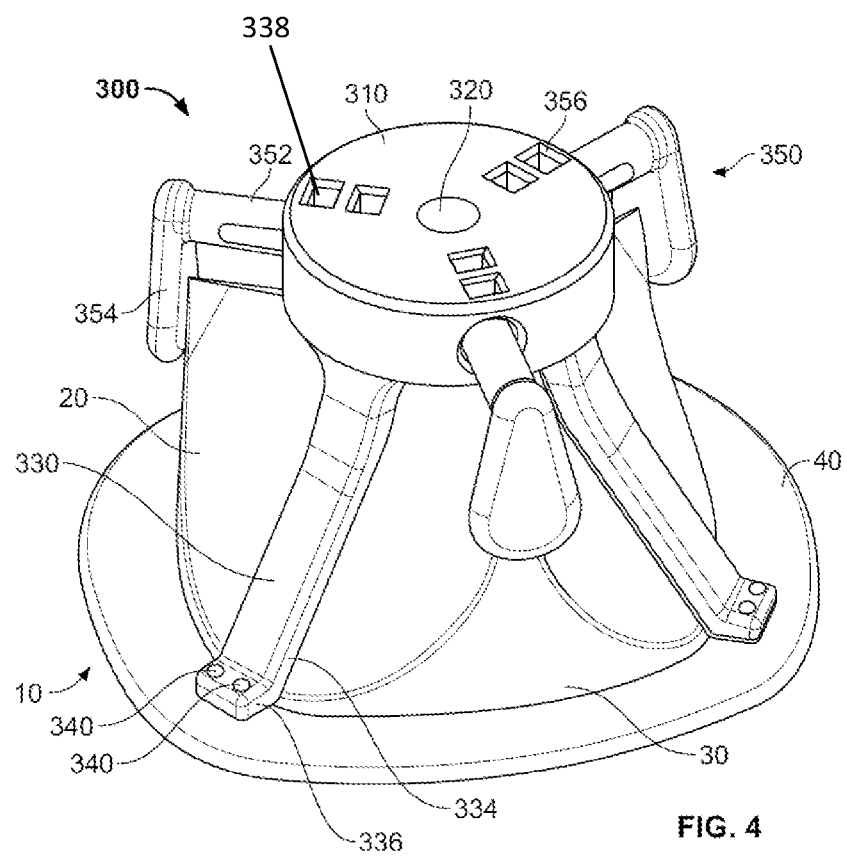
FIG. 4 is a top perspective view of an embodiment of a valve holder in partial phantom lines coupled to the valve of FIG. 1.
Figure 5A:
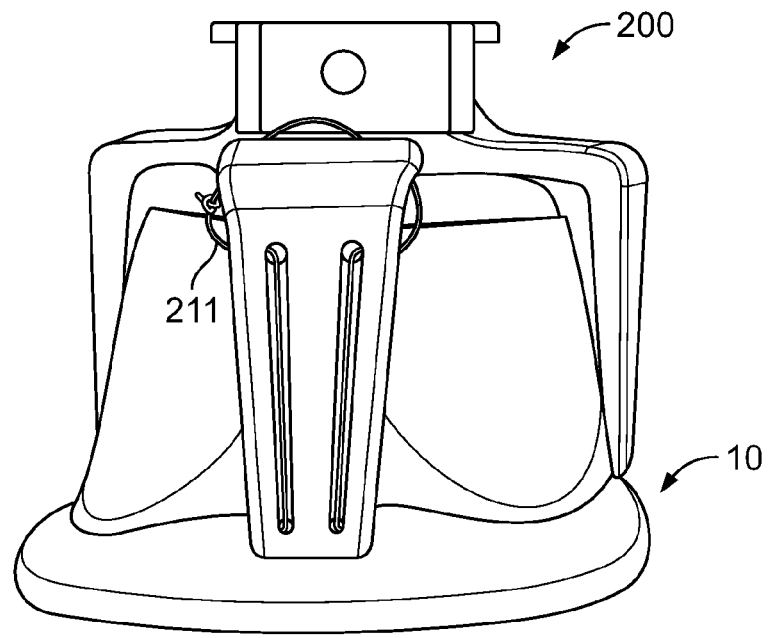
FIGS. 5A-B are side and top views of the combination valve and valve holder of FIG. 2.
Figure 5B:
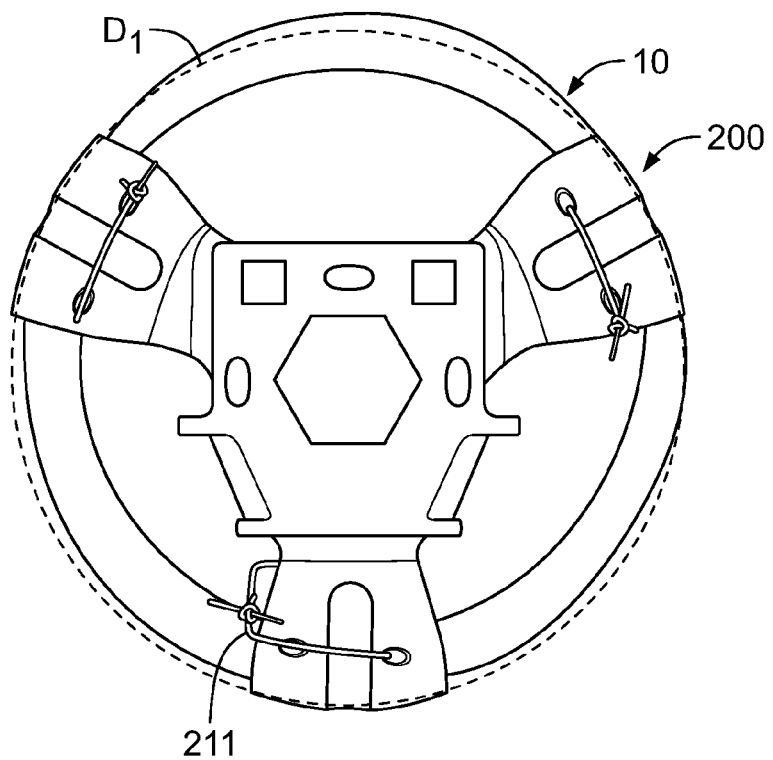
Figure 5C:
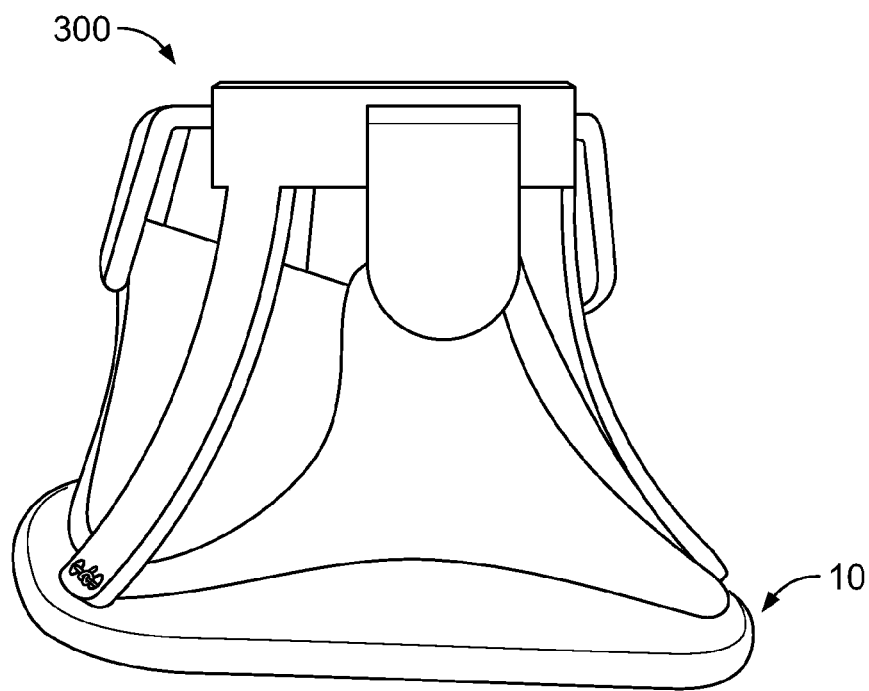
FIGS. 5C-D are side and top views of the combination valve and valve holder of FIG. 4.
Figure 5D:
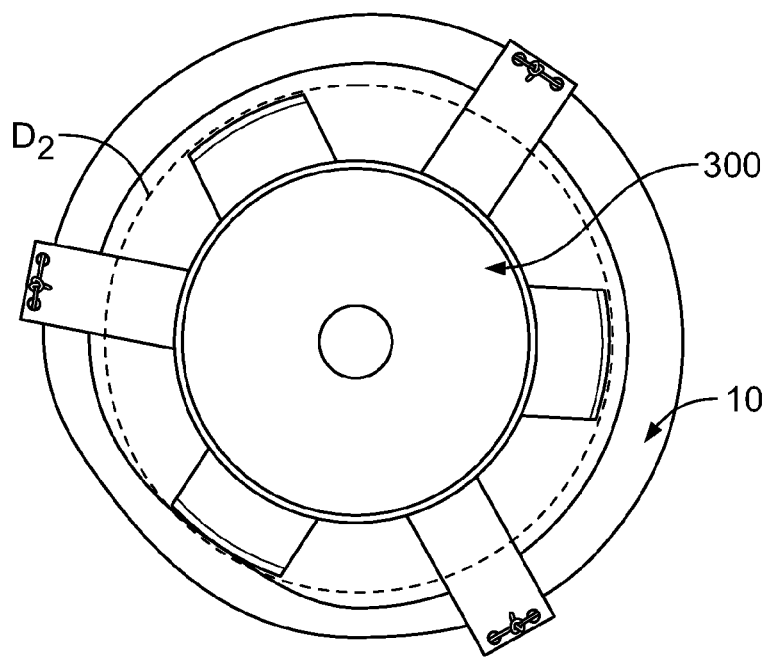

FIG. 4 illustrates a valve holder 300 according to an embodiment of the invention coupled to prosthetic heart valve 10. Valve holder 300 includes a generally cylindrical base 310 having a central aperture 320 for accepting the shaft of an elongated handle (not shown). A plurality of legs 330 extend downward and radially outward from the base 310. Three legs 330 are illustrated in this particular embodiment, but more or fewer legs may be provided depending on the number of leaflets in the particular prosthetic valve being implanted. The legs 330 are dimensioned to extend from the base 310 adjacent the outflow portion of the valve 10 to free ends 334 intended to lie adjacent cuff 40 when the valve holder 300 is assembled to the valve. The free ends 334 of the legs 330 may include an outwardly directed flange 336 which may include one or more apertures 340. To fix the valve holder 300 to the valve 10, sutures may be passed through the apertures 340 and through the cuff 40. When the valve holder 300 is coupled to the valve 10, the legs 330 generally run down cusps of the leaflets 20 between the commissure posts 30, and the flanges 336 of the legs 330 are generally parallel to the cuff 40. The legs 330 may be generally straight or may be curved to follow the contour of a respective valve leaflet 20.

Valve holder 300 also includes a plurality of fingers 350. While there are three fingers 350 in the illustrated embodiment, a greater or lesser number of fingers may be provided depending on the number of commissure posts 30 in the particular prosthetic valve being implanted. Each finger 350 may include a rod-like portion 352 extending radially outward from an inner end fitted into a correspondingly shaped bore in the annular sidewall of base 310 to an outer end. A tip 354 may extend downwardly from the outer end of rod-like portion 352 in a direction generally perpendicular thereto. At its inner end, rod-like portion 352 may include a tab or protrusion 338 that projects in a direction opposite to tip 354. More particular, protrusion 338 projects toward the inner flat surface of base 310. In FIG. 4, the protrusion 338 is not visible but is located in the base 310 in contact with a recess 356, described more fully below.

The inner flat surface of base 310 may include multiple series of notches or recesses 356, with each series arranged in a linear array radially aligned with the rod-like portion 352 of a finger 350. Preferably, recesses 356 are sized and shaped to receive the protrusions 338 on rod-like portions 352, thereby defining discrete positions at which the radial extension of fingers 350 is locked relative to base 310.

For example, when the protrusion 338 of a finger 350 is in the outermost recess 356, the tip 354 of that finger may just barely contact a commissure post 30 without exerting much (or any) force on the particular commissure post. The finger 350 may be pushed radially inwardly toward the center of the base 310, with the applied force overcoming the engagement of protrusion 338 in recess 356, until the protrusion mates with another recess closer to the center of the base 310. In this new position, the tip 354 of the finger 350 applies more force to the particular commissure post 30, causing the commissure post to deflect radially inwardly.

The protrusions 338 may have a pawl shape such that the protrusions and the recesses 356 together act as a ratcheting mechanism. In such arrangement, the fingers 350 may be pushed radially inwards toward the center of base 310 relatively easily to deflect the commissure posts 30 while resisting movement in the opposite direction. As a result, the inward deflection of the commissure posts 30 is generally irreversible until the holder 300 is removed from the valve 10.

Although FIG. 4 illustrates holder 300 as having two recesses 356 for each finger 350, more recesses may be provided for each finger so as to define additional positions at which the radial extension of the fingers may be locked relative to base 310. As a result of these additional positions, the commissure posts 30 may be deflected inwardly in more gradual increments. Further, since each finger 350 may move independently of the other fingers, each finger may deflect its respective commissure post 30 to a different degree. This independence of operation, as well as the provision of multiple recesses 356 for each finger 350, allows the surgeon a large degree of choice in determining how the valve 10 is to be constricted during an implantation procedure.

FIGS. 5A-D depict valve holders 200 and 300 connected to the same size valve 10 in side-by-side views. As can be seen, particularly from comparing FIGS. 5B and 5D, valve holder 300 has a smaller effective diameter $D_2$ at the outflow end of the valve 10 when the valve is constricted compared with the effective diameter $D_1$ of valve holder 200 at the outflow end of the valve. For example, valve holder 200 may have an effective diameter $D_1$ of approximately 27.0 mm at the outflow end of a 23 mm valve. When in the most constricted configuration, valve holder 300 may have an effective diameter $D_2$ of approximately 22.5 mm at the outflow end of a 23 mm valve. This smaller diameter may make it easier for a surgeon to work in the surgical field during implantation of valve 10.

Figure 6A:
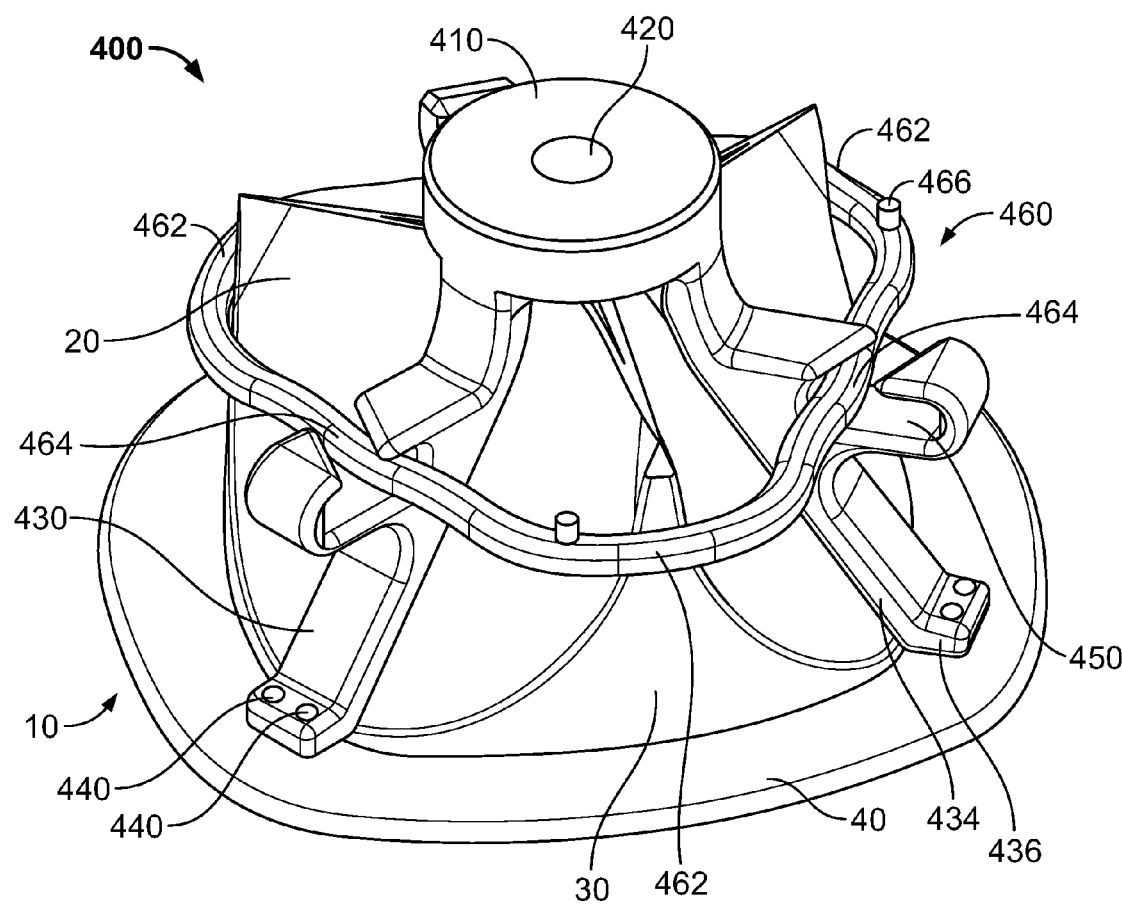
FIG. 6A is a top perspective view of yet another embodiment of a valve holder coupled to the valve of FIG. 1.

FIG. 6A illustrates a further embodiment of a valve holder 400 coupled to the prosthetic heart valve 10. Valve holder 400 is similar to valve holder 300 in many respects. For example, valve holder 400 includes a generally cylindrical base 410 having a central aperture 420 for accepting the shaft of an elongated handle (not shown). A plurality of legs 430 extend downward and radially outward from the base 410. Three legs 430 are illustrated in this particular embodiment, but a greater or lesser number of legs may be provided depending on the number of leaflets in the prosthetic valve being implanted. The legs 430 are dimensioned to extend from the base 410 adjacent the outflow portion of the valve 10 to free ends 434 intended to lie adjacent cuff 40 when the valve holder 400 is assembled to the valve. The free ends 434 of the legs 430 may include an outwardly directed flange 436 which may include one or more apertures 440. To fix the valve holder 400 to the valve 10, sutures may be passed through the apertures 440 and through the cuff 40. When the valve holder 400 is coupled to the valve 10, the legs 430 generally run down cusps of the leaflets 20 between the commissure posts 30, and the flanges 436 of the legs 430 are generally parallel to the cuff 40. The legs 430 may be straight or may be curved to follow the contour of a respective valve leaflet 20.

Figure 6B:
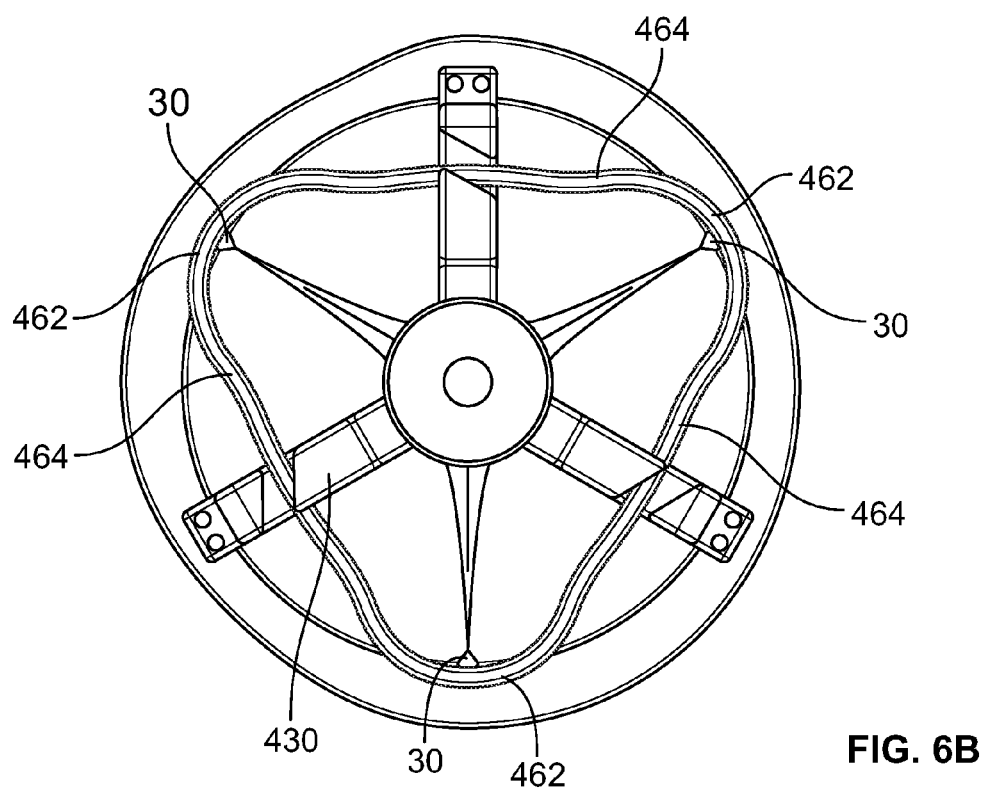
FIGS. 6B-C are top views of the combination valve and valve holder of FIG. 6A in unconstricted and constricted configurations, respectively.
Figure 6C:
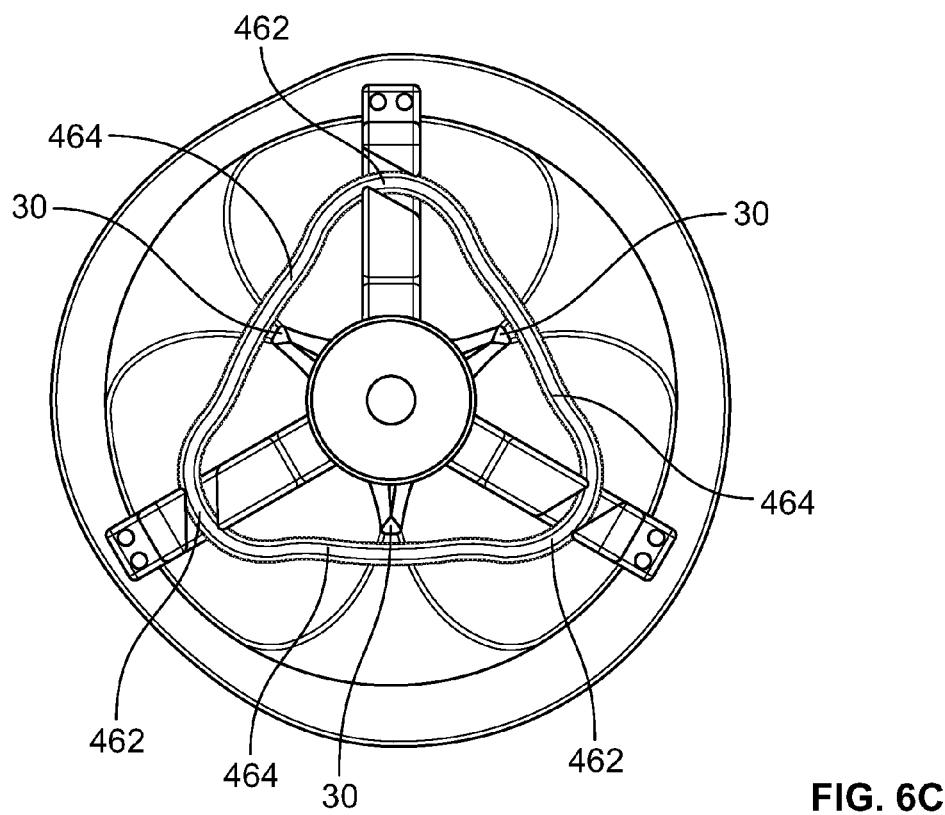

A ring holder 450 projects radially outward from each leg 430 at about the midpoint between base 410 and the flange 436 at the end of the leg. Ring holders 450 are fully enclosed on three sides and have an open slot 452 on a side facing toward base 410. A wire ring 460 may be assembled in ring holders 450 so as to be rotatable relative to legs 430 about an axis passing through the center of base 410. The wire ring 460 has a generally triangular shape with three substantially straight sides 464 joined by rounded connectors 462. As a result of its triangular configuration, the distance between the center of the wire ring 460 and the rounded corners 462 is greater than the distance between the center of the wire ring and the substantially straight sides 464. When wire ring 460 is rotated to an unconstricted configuration as illustrated in FIGS. 6A and 6B, the rounded connectors 462 are radially aligned with the commissure posts 30. Because the distance between the center of wire ring 460 and the connectors 462 is about equal to or greater than the distance between the center of valve 10 and the unconstricted commissure posts 30, the rounded connectors may barely contact the commissure posts in this position, and thus apply little or no inward pressure to the commissure posts. When the wire ring 460 is rotated 60° to a constricted configuration as illustrated in FIG. 6C, the substantially straight sides 464 of the ring are radially aligned with the commissure posts 30. Because the distance between the center of wire ring 460 and sides 464 is less than the distance between the center of valve 10 and the unconstricted commissure posts 30, the sides of the ring contact the commissure posts and deflect them radially inwardly. To facilitate the rotation of wire ring 460 relative to legs 430, one or more bosses 466 may be provided on the wire ring for the user to grasp. Alternately, a tool (not illustrated) may be provided to releasably connect to the bosses 466 to facilitate rotation. For example, such a tool may be a generally hollow cylinder with recesses in the wall of the cylinder corresponding to the location of the bosses 466. Although the wire ring 460 is illustrated as having a triangular shape, other shapes may be effective to achieve a similar result. For example, a generally elliptically shaped wire ring may be effective to constrict a valve with two coapting leaflets and two commissure posts.

Figure 7A:
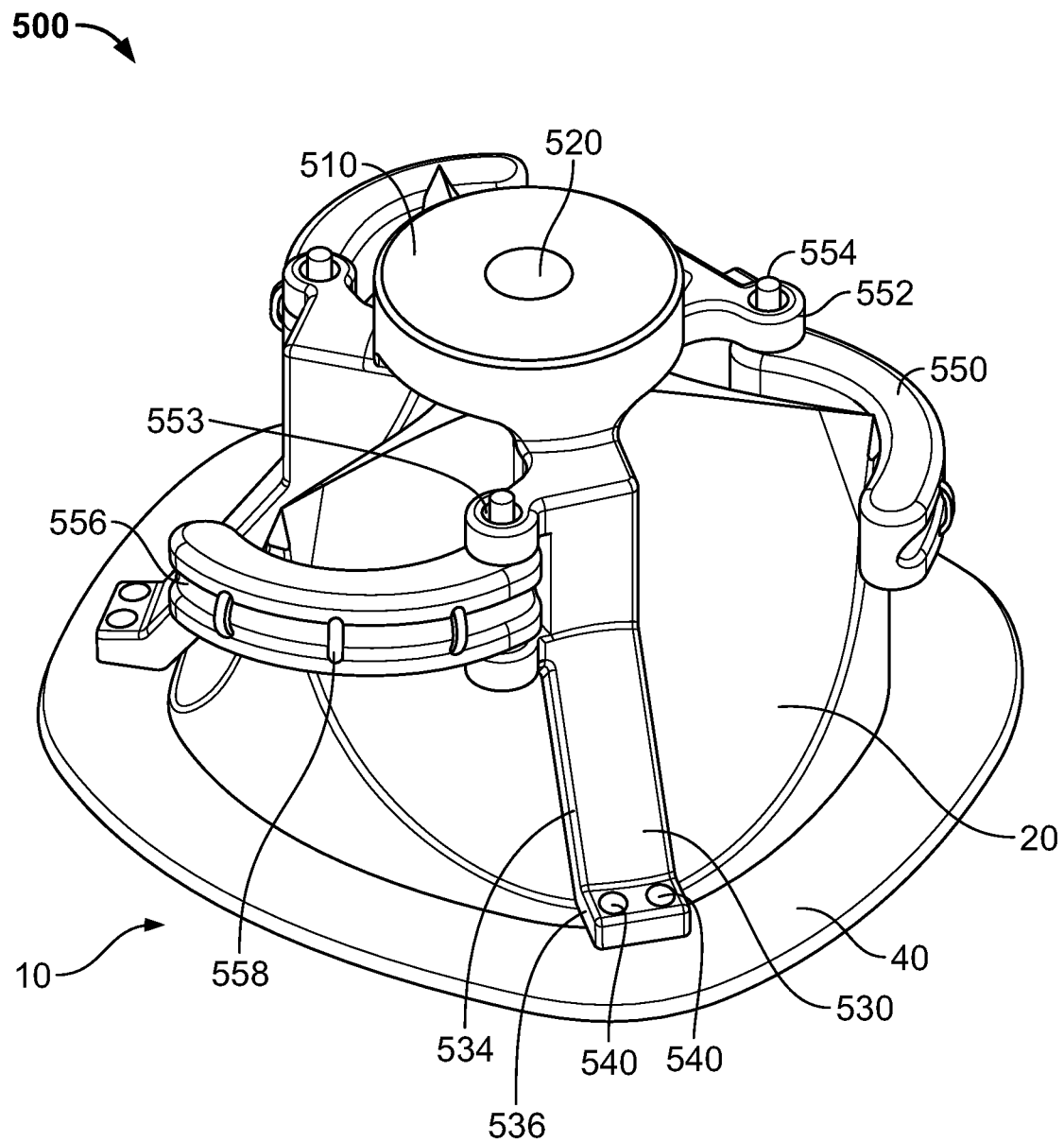
FIG. 7A is a top perspective view of a further embodiment of a valve holder coupled to the valve of FIG. 1.

FIG. 7A illustrates yet a further embodiment of a valve holder 500 coupled to the prosthetic heart valve 10. Valve holder 500 is similar to valve holders 200, 300 and 400 in many respects. For example, valve holder 500 includes a generally cylindrical base 510 having a central aperture 520 for accepting the shaft of an elongated handle (not shown). A plurality of legs 530 extend downward and radially outward from the base 510. Although this particular embodiment shows three legs 530, a greater or lesser number of legs may be provided depending on the number of leaflets in the prosthetic valve being implanted. The legs 530 are dimensioned to extend from the base 510 adjacent the outflow portion of the valve 10 to free ends 534 intended to lie adjacent cuff 40 when the valve holder 500 is assembled to the valve. The free ends 534 of the legs 530 may include an outwardly directed flange 536 which may include one or more apertures 540. To fix the valve holder 500 to the valve 10, sutures may be passed through the apertures 540 and through the cuff 40. When the valve holder 500 is coupled to the valve 10, the legs 530 generally run down cusps of the leaflets 20 between the commissure posts 30, and the flanges 536 of the legs 530 are generally parallel to the cuff 40. The legs 530 may be straight or may be curved to follow the contour of a respective valve leaflet 20.

The valve holder 500 includes a plurality of generally arcuate fingers 550, with each finger projecting laterally from a leg 530 at a point just below the point at which the leg joins base 510. In that regard, each leg 530 may include a pair of laterally projecting spaced tabs 552 each having an aperture 553 therein. One end of each finger 550 may include a transverse through bore (not shown). The end of finger 550 may be inserted between tabs 552 with the through bore aligned with apertures 553. A pin 554 extending through the apertures 553 and the through bore in the finger 550 may pivotally join the finger to leg 530. Fingers 550 may be joined to legs 530 so that, when holder 500 is mounted to a valve 10, the concave sides of the fingers face toward the valve with the free ends of the fingers disposed radially outward of the commissure posts 30.

Figure 7B:
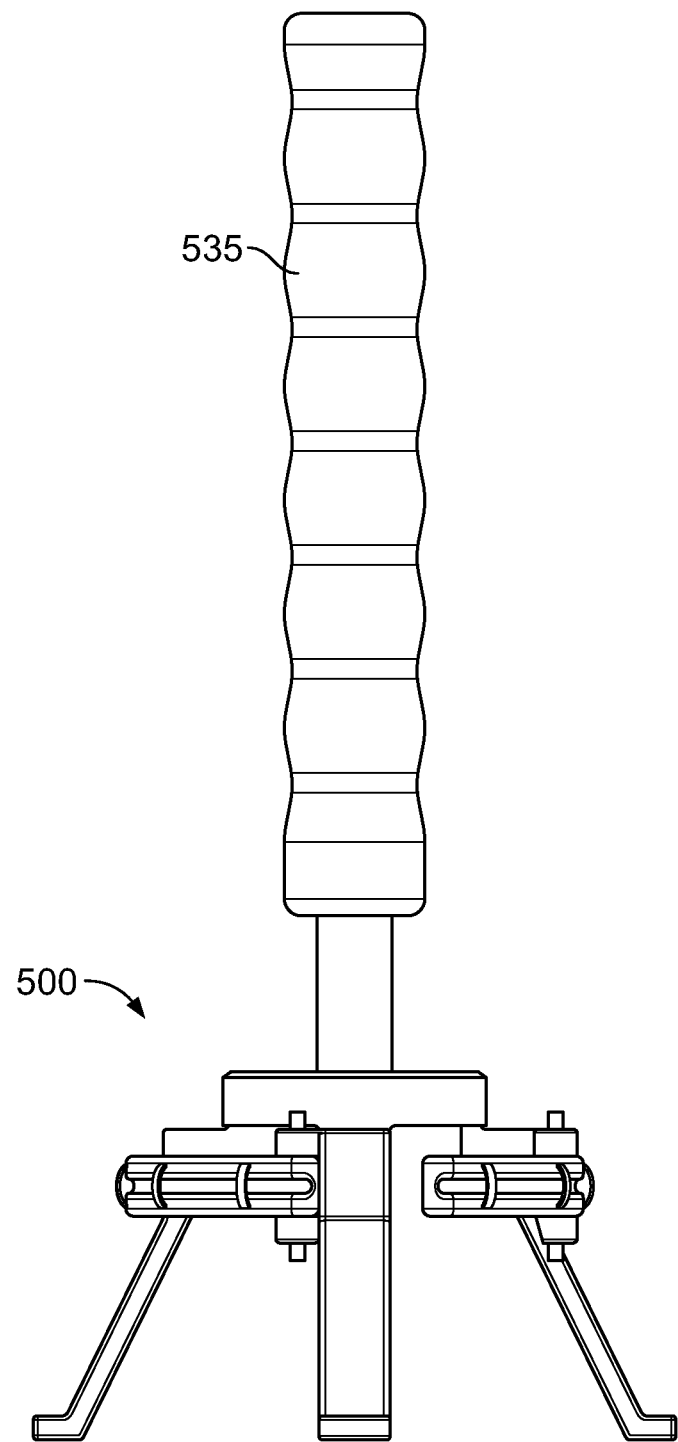
FIG. 7B is a side view of a handle attached to the valve holder of FIG. 7A.

The outer convex surface of each finger 550 may include a groove 556, with one or more retaining features 558 extending across the groove. One or more sutures (not illustrated) may be threaded under retaining features 558 and through the grooves 556 before coupling to a handle 535, shown in FIG. 7B. In one arrangement, a length of suture may be threaded from the free end of one finger 550 under the retaining features 558 and through the groove 556 of the finger, around the retaining feature farthest from the free end of the finger, and then back over the retaining features to the free end of the finger. The two free ends of the suture may then be coupled to handle 535 so that the suture wraps around a shaft or other structure of the handle and is drawn in as the handle is rotated. As the suture is drawn in, it exerts a radially inward force on the free end of the finger 550 to which it is attached, causing the finger to pivot radially inwardly and to simultaneously deflect the adjacent commissure post 30 radially inwardly to a constricted condition. A similar length of suture may couple each of the other fingers 550 to the handle 535 and may operate in the same manner to draw the other fingers radially inwardly, and with them, the other commissure posts 30.

In a similar embodiment, one (or more) sutures may extend to the top base 510 the holder 500 around a spool feature in the base 510. That spool feature may be rotated by a user via the handle similar to that shown in FIG. 3. As the spool rotates, it takes up the suture and thus pulls the fingers radially inward to deflect the commissure posts 30. The spool feature may also contain a ratchet mechanism that allows the user to remove the handle and keep the fingers 550 and commissure posts 30 constricted. After implantation, the suture coupled to the fingers 550 may be cut to release the fingers 550 from the restricted configuration. Alternately or in addition, the user may cut the suture connecting the legs 530 of the holder 500 to the cuff 40 of the valve 10 to release the holder from the valve.

In another arrangement, rather than looping around the retaining feature 558 farthest from the free end of a finger 550, one end of the length of suture may be secured to that retaining feature or to another point on the finger with the suture extending around the free end of the finger. The other end of the suture may be coupled to handle 535 for takeup by the handle as it is rotated, thereby pivoting the finger radially inwardly and simultaneously deflecting the adjacent commissure post 30 radially inwardly to the constricted condition.

In a still further arrangement, a single length of suture may be coupled to all of the fingers 550 and to handle 535. More particularly, one end of the length of suture may be secured to a retaining feature 558 or other structure on a first finger 550. That length of suture may then be threaded under the other retaining features 558 and through the groove 556 toward the free end of that first finger 550. The suture may then be directed to the connected or pivoting end of the next adjacent finger 550, and under the retaining features 558 and through the groove 556 of that finger toward its free end. This suture threading procedure may be repeated for the other two fingers 550, following which the free end of the suture may be coupled to handle 535. As the handle 535 is rotated, the suture will wrap around a shaft or other structure of the handle and cause each of fingers 550 to pivot radially inwardly. The inward pivoting of fingers 550 will simultaneously deflect the adjacent commissure posts 30 radially inwardly to the constricted condition.

In each of the arrangements described above, the handle 535 may include a known type of ratcheting mechanism so that, if the handle is released after inward deflection of the commissure posts 30, 10, the handle does not rotate in the opposite direction to unwind the suture and thereby release the commissure posts 30 from the constricted condition. Also, as described above, the holders themselves may include a ratcheted spool mechanism. This may be preferable over a spool and ratcheting mechanism in the handle 535 as the handle 535 may be removed without disturbing the position of the spool and ratcheting mechanism in the holder.

Figure 7C:
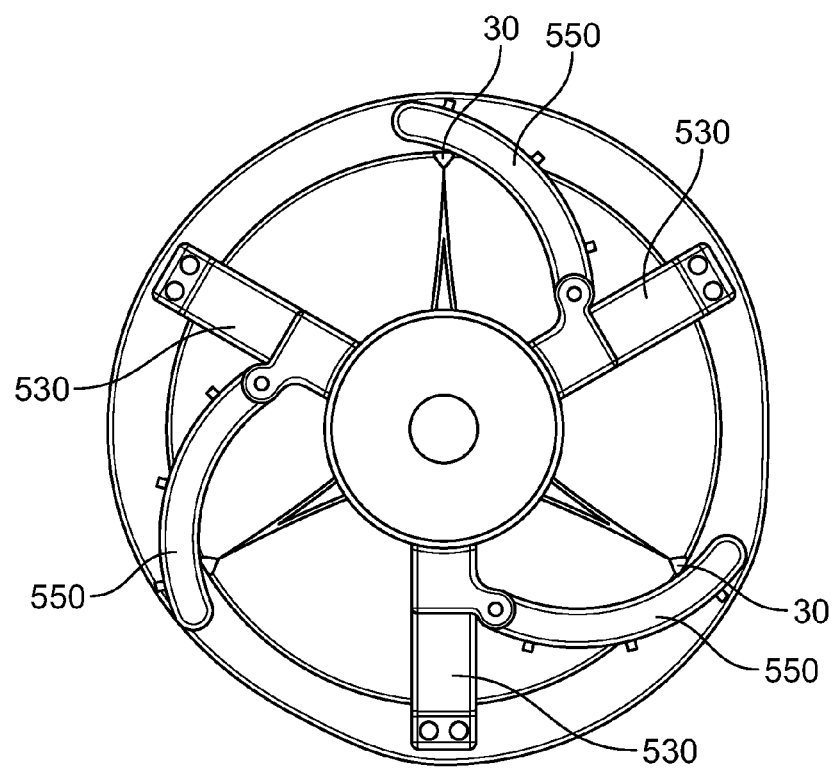
FIGS. 7C-D are top views of the combination valve and valve holder of FIG. 7A in unconstricted and constricted configurations, respectively.
Figure 7D:
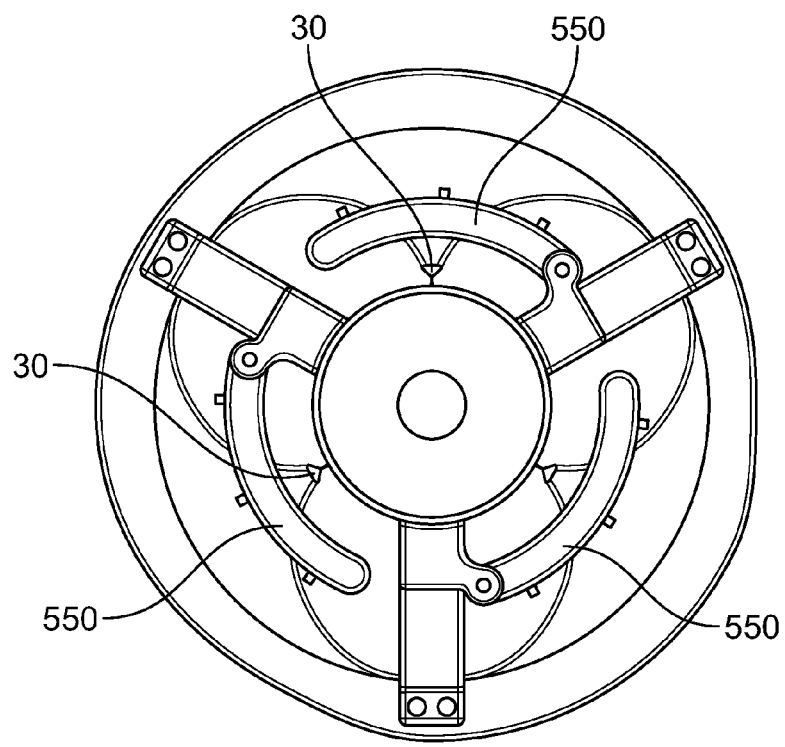

FIG. 7C is a top view of the valve holder 500 and valve 10 in an unconstricted configuration prior to the suture being spooled onto the handle 535. FIG. 7D is a top view of the valve holder 500 and valve 10 in a constricted configuration after the suture has been spooled onto the handle 535, pulling the fingers 550 and the commissure posts radially inward. In each of the arrangements described above, fingers 550 protect the tissue portions of valve 10, preventing the suture from cutting or otherwise damaging the leaflets 20 or other portions of valve tissue.

Figure 7E:
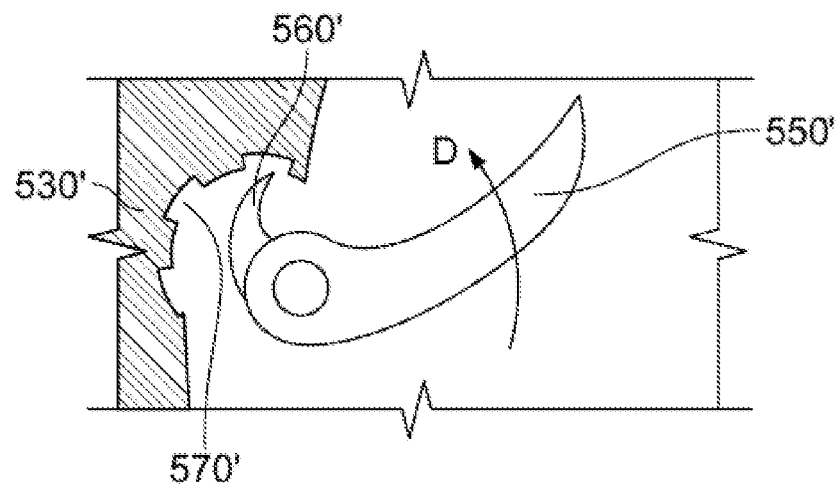
FIG. 7E is an enlarged partial top view of an alternate embodiment of a finger and leg of the valve holder of FIG. 7A.

Generally, the inward deflection or constriction described in connection with valve holder 500 in FIGS. 7A-D causes simultaneous constriction of each commissure post 30 as the suture is spooled onto the handle 535. In a variant of valve holder 500, each of fingers 550' may have a ratcheting mechanism 560', as illustrated in FIG. 7E. Ratcheting mechanism 560' eliminates the need for any sutures, and allows for independent inward deflection of each finger 550' and the commissure post 30 associated therewith. Generally, fingers 550' are identical to fingers 550, except the connected or pivoting end of fingers 550' include a pawl 560'. Each leg 530' includes a plurality of teeth 570' positioned between the tabs (not shown in this embodiment) to which the finger is pivotally connected. As the finger 550' is pivoted radially inwardly in the direction of arrow D, the pawl 560' will engage successive teeth 570'. The pawl 560' and teeth 570' may have a ratcheting relationship such that the finger 550' may pivot in the radially inward direction D, but not in the reverse direction. A stop (not illustrated) may be provided on the leg 530' after a final tooth 570' such that the finger 550' may pivot radially inward by only a predetermined amount. With this configuration, a user may manually manipulate each finger 550' to inwardly deflect each commissure post 30 independently to a desired level of constriction and hold it in the constricted condition during the implantation procedure.

Figure 8A:
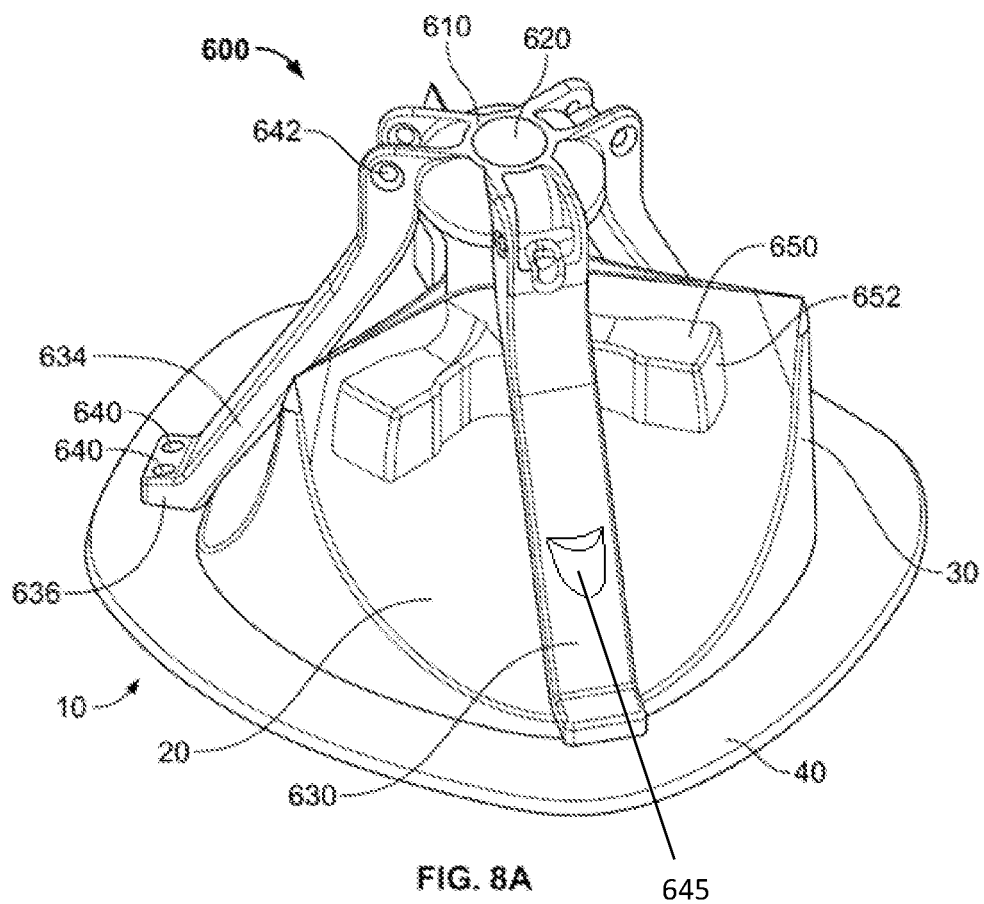
FIG. 8A is a top perspective view of a still further embodiment of a valve holder coupled to the valve of FIG. 1.

FIG. 8A illustrates still another embodiment of a valve holder 600 coupled to a prosthetic heart valve 10. The valve 10 is shown as partially transparent to illustrate portions of the valve holder 600 located within the valve. Valve holder 600 is similar to valve holders 200, 300, 400 and 500 in many respects. For example, valve holder 600 includes a generally cylindrical or hemispherical base 610 having a central aperture 620 for accepting the shaft of an elongated handle (not shown). A plurality of legs 630 extend downward and radially outward from the base 610. Three legs 630 are illustrated in this particular embodiment, but the valve holder 600 may include a greater or lesser number of legs depending on the number of leaflets in the prosthetic valve being implanted. The legs 630 are dimensioned to extend from the base 610 adjacent the outflow portion of the valve 10 to free ends 634 intended to lie adjacent cuff 40 when the valve holder 600 is assembled to the valve. The free ends 634 of the legs 630 may include an outwardly directed flange 636 which may include one or more apertures 640. To fix the valve holder 600 to the valve 10, sutures may be passed through the apertures 640 and through the cuff 40. Apertures 642 may also be included in legs 630 adjacent base 610. If desired, the suture connecting the cuff 40 to the legs 630 through apertures 640 may extend further across apertures 642. By using these extra apertures 642, the suture extends across a gap closer to the surgeon than the sutures in the cuff 40. This allows a surgeon to release the valve holder 600 form the valve 10 by cutting the suture where it extends through apertures 642. This may be more convenient than if the surgeon attempted to cut a suture only attached to cuff 40 with apertures 640. This or similar features may be added to other embodiments of valve holders described herein to facilitate easy release of the valve 10 from the particular valve holder. When the valve holder 600 is coupled to the valve 10, the legs 630 generally run down cusps of the leaflets 20 between the commissure posts 30, and the flanges 636 of the legs 630 are generally parallel to the cuff 40. The legs 630 may be generally straight or may be curved to follow the contour of a respective leaflet 20 of the valve 10.

Valve holder 600 further includes a hub 650 intended to be positioned below leaflets 20 of valve 10, and to project upward through the interface between the leaflets for connection to the underside of base 610. The hub 650 includes a plurality of pads 652 extending radially outward therefrom. In the illustrated embodiment, the hub 650 includes three pads 652, but a greater or lesser number of pads may be provided depending on the number of leaflets in the valve being implanted. When the valve holder 600 is coupled to the valve 10, the pads 652 are configured to extend radially outward, each pad extending toward a respective commissure post 30. The pads 652 are dimensioned such that they do not extend fully to their respective commissure posts 30, but rather define a gap between the ends of the pads and the commissure posts. For example, the diameter of the commissure posts may be approximately 20 mm and the diameter of a circle defined by the outer surfaces of the pads 652 may be approximately 18 mm, leaving a gap of about 2 mm therebetween.

In operation, valve holder 600 does not significantly change the outer diameter of the valve 10 since it does not include any mechanisms for inwardly deflecting the commissure posts 30. In addition, the configuration and positions of the pads 652 allows for only limited inward deflection of the commissure posts 30 during implantation. For example, if the valve 10 is passed through a tube or other constricted area and inward forces are applied to the commissure posts 30, the commissure posts may deflect inwardly only until contacting a respective pad 652. Similarly, a user may manually deflect the commissure posts 30 during implantation only up to the point at which the commissure posts contact their respective pads 652. This type of inward deflection may be referred to as passive constriction. In addition to the benefits of a small profile and the provision of support to the leaflets, the valve holder 600 may be connected to valve 10 prior to storage of the valve, such that the end user need not assemble the valve holder to the valve. This is due, at least in part, to the fact that the pads 652 do not exert any force on the commissure posts 30 when the valve is in an unconstricted state. This reduces or eliminates the likelihood that the valve 10 will be deformed by the holder 600 during storage prior to use.

Each leg 630 may optionally include a pocket 645. The pocket 645 is generally defined by an inner wall and an outer wall. The inner wall may be the leg 630, with the outer wall extending out from the leg 630. Alternatively, the inner wall may be defined by a recess in the leg 630, with the space between the inner wall recess and leg 630 defining the pocket. In either case, a pocket 645 is formed in the leg 630 that may function to accept a tool, such as forceps or another guiding tool. One benefit of having one or more pockets 645 is that, during insertion of the valve, it surgeon may wish to grab the valve holder 600 manually or with a tool to facilitate positioning of the valve 10. The pockets 645 may accept forceps (or other tools) to facilitate the surgeon's ability to more precisely guide the valve 10 and valve holder 600. Particularly, this may be useful for valves 10 with tissue leaflets on the outer surfaces, as any handling, especially forceful handling, of the outer tissue surface of the valve 10 may compromise the valve. With the addition of one or more pockets 645, the surgeon may more easily guide the valve 10 into its proper position. Pockets 645 may also be provided with other embodiments of valve holders described herein.

Figure 8B:
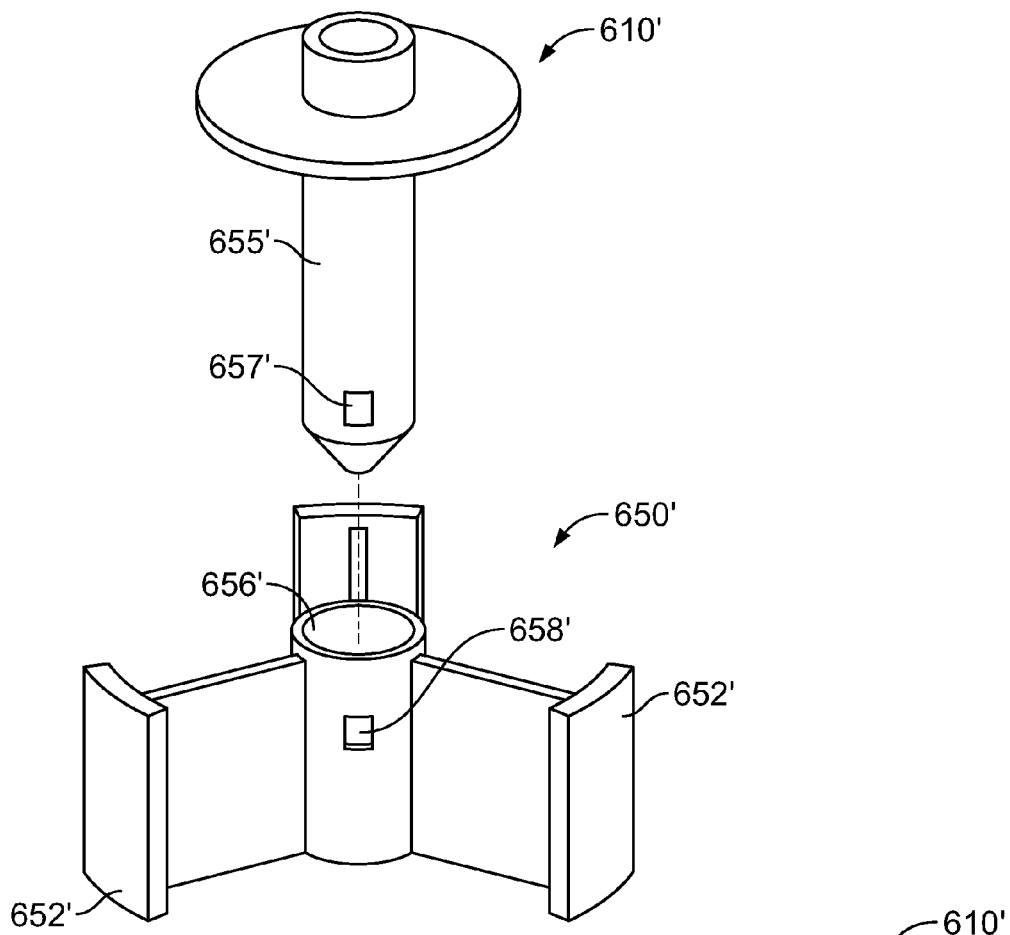
FIG. 8B is an exploded view of an alternate embodiment of a hub component of the valve holder of FIG. 8A.
Figure 8C:
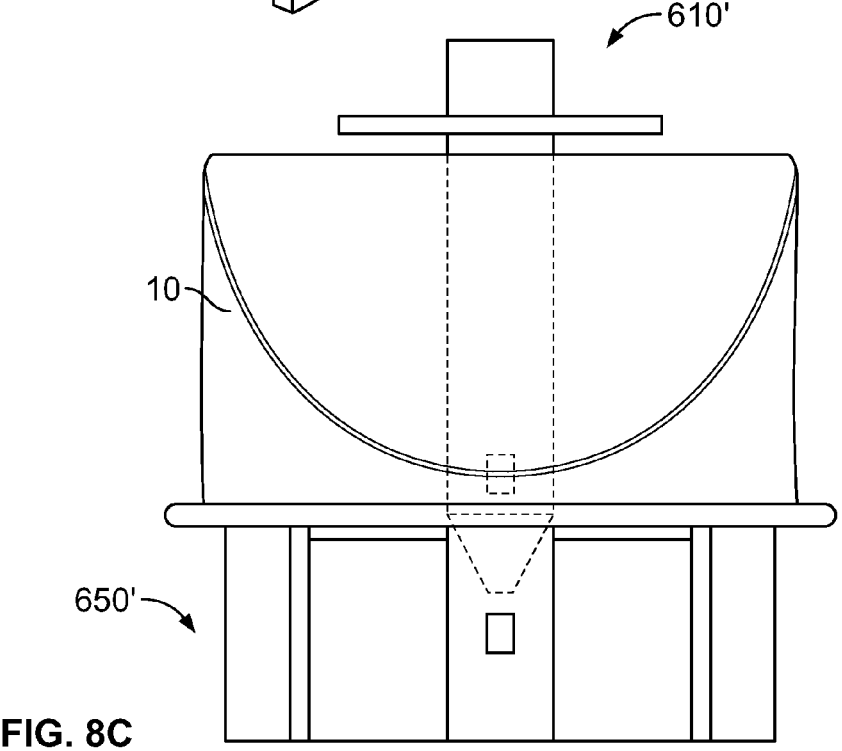
FIG. 8C is a side view showing the assembly of the valve of FIG. 1 to the hub component of FIG. 8B.

An alternate embodiment of the base 610 and hub 650 is illustrated in FIGS. 8B-C. The hub 650' has a plurality of radially projecting pads 652' which are similar to pads 652 of valve holder 600. That is, pads 652' project toward the commissure posts 30 of valve 10 when hub 650' is connected to the valve, but are spaced therefrom so as to define a gap between the ends of the pads and the commissure posts. Although three pads 652' are shown on hub 650', a greater or lesser number of pads may be provided depending on the number of leaflets in the valve being implanted. A plurality of legs, similar to legs 630 of valve holder 600, extend from base 610' but have been omitted in the illustration for clarity. Base 610' includes a generally cylindrical shaft 655' configured for insertion into a corresponding bore 656' in the hub 650'. Shaft 655' may include a resilient tab 657' configured to snap into a similarly shaped aperture 658' in the hub 650' to lock the base 610' to the hub. This two-piece configuration may be useful so that the hub 650' may be inserted into the valve 10 through the inflow end, and the base 610' may be passed through the outflow end of the valve, as illustrated in FIG. 8C, for connection to the hub. Assembling the valve holder in this manner may be easier than attempting to insert the entire holder through the inflow or outflow portion of the valve 10. This embodiment may also be of further benefit by reducing extended contact of the pads 652' with the tissue of leaflets 20 during extended storage. Preferably, the valve 10 and holder may be stored together for upwards of three years without any or significant detrimental effect on the valve 10 due to the holder, and particularly the pads 652'.

Figure 9:
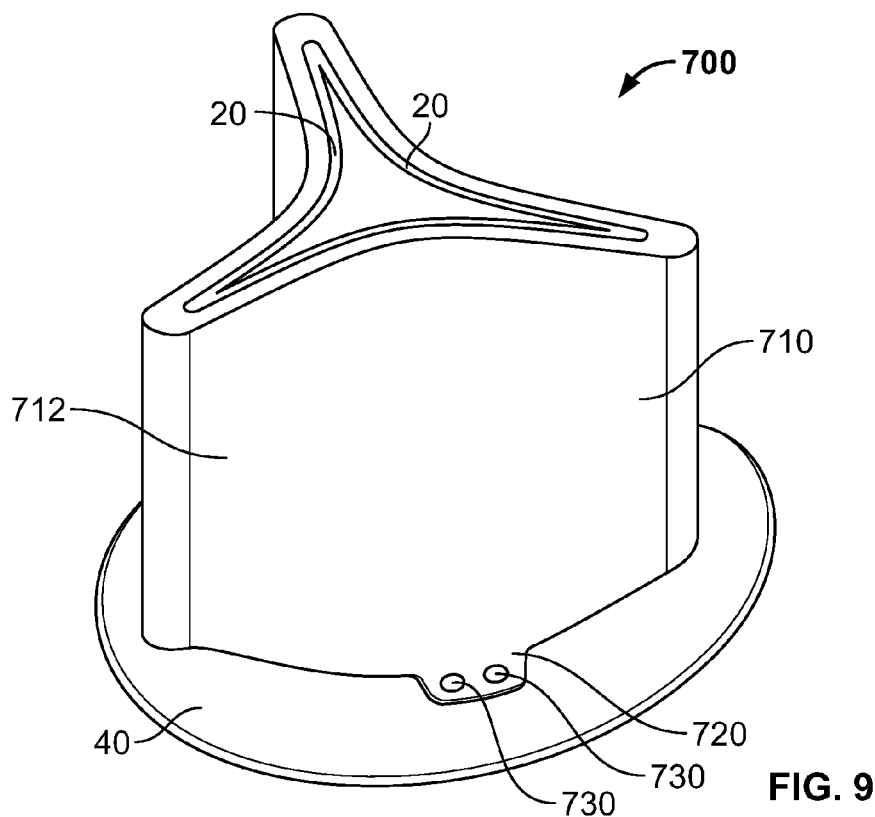
FIG. 9 is a top perspective view of yet another embodiment of a valve holder coupled to the valve of FIG. 1.

FIG. 9 illustrates yet a further embodiment of a valve holder 700. Valve holder 700 includes a shield 710 having three generally upright curved walls 712 that conform to the shape of the leaflets 20 when the leaflets are in a mostly or fully coapted condition. The shield 710 may be formed of a polymer or any other suitable material, preferably as a single continuous structure, and acts to protect the tissue leaflets 20 as well as other structural components of the valve 10, such as a stent, during implantation of the valve 10. A plurality of flanges 720 are spaced around the bottom circumference of the shield 710, each flange having apertures 730. Similar to other embodiments described above, a suture may be passed through the apertures 730 into the cuff 40 to secure the valve holder 700 to the valve 10. Although not illustrated, the top of the shield 710 may include a base similar to other embodiments described above for attaching a handle to the valve holder 700.

Figure 10A:
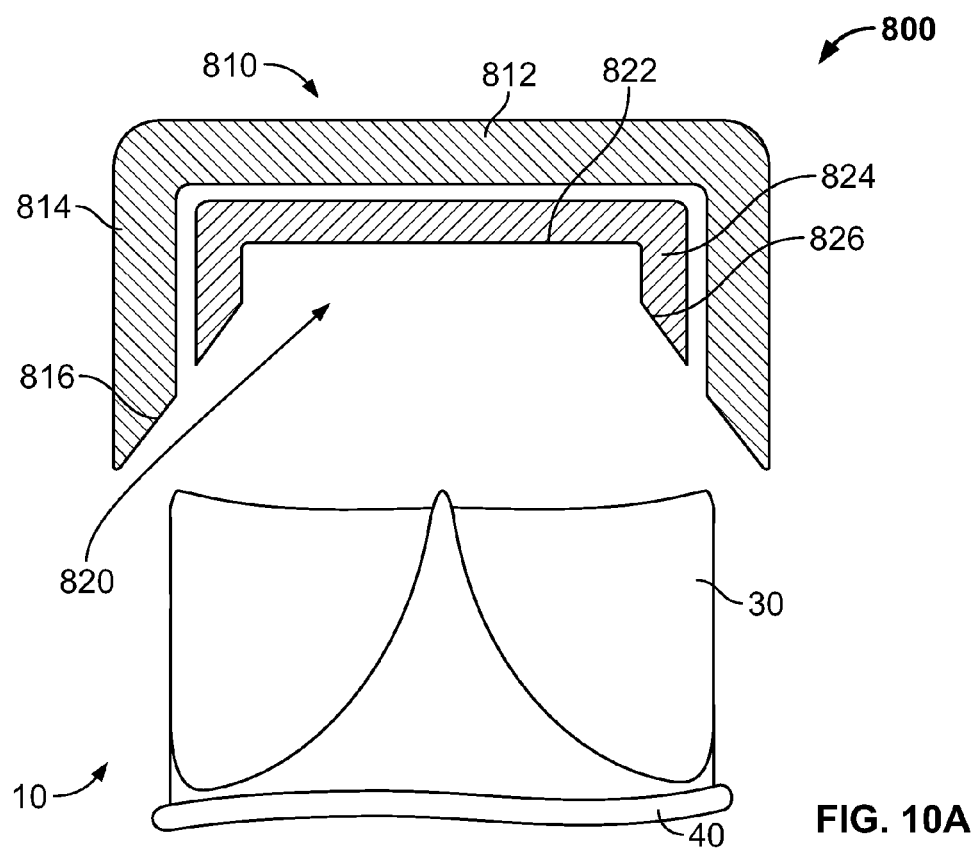
FIG. 10A is a cross-sectional view of a further embodiment of a valve holder before it is coupled to the valve of FIG. 1.

FIG. 10A illustrates a cross-sectional view of a further embodiment of a valve holder 800. In the illustrated embodiment, valve holder 800 includes a generally cylindrical outer body 810 having a circular top 812 with a cylindrical wall 814 depending therefrom. The free end of the cylindrical wall 814 is tapered such that the outermost surface of the wall extends farther from the circular top 812 than the innermost surface of the wall. This tapered end of wall 814 forms a first guide surface 816. Valve holder 800 also includes a generally cylindrical inner body 820 which is substantially identical to, but smaller than, the outer body 810. The inner body 820 has a circular top 822 with a cylindrical wall 824 depending therefrom. The free end of the wall 824 is also tapered similarly to the free end of cylindrical wall 814 to form a second guide surface 826.

Figure 10B:
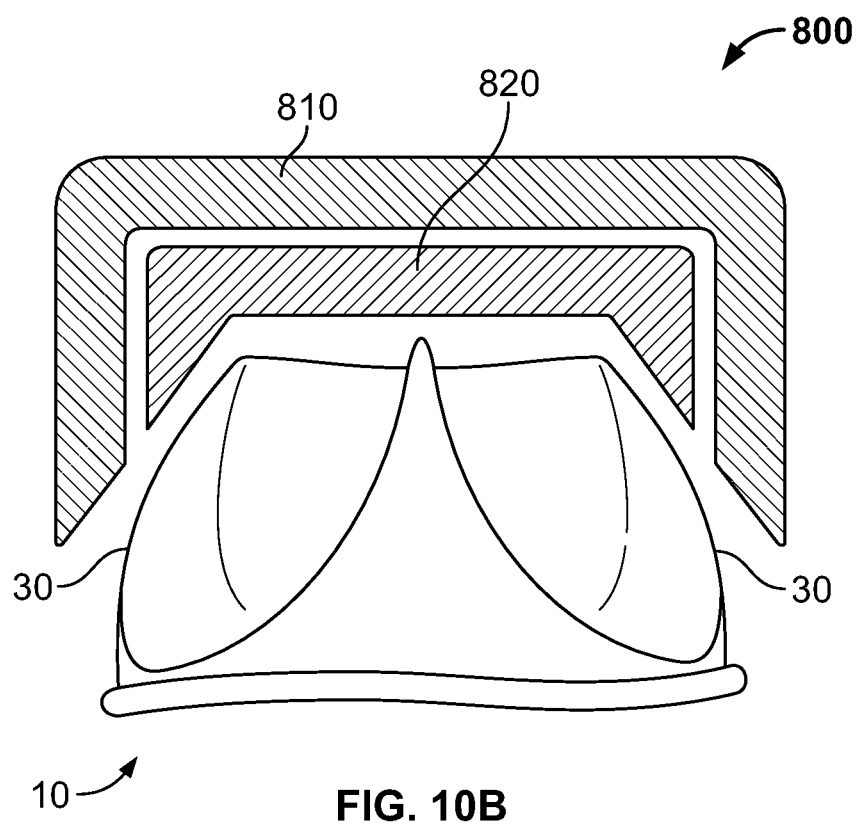
FIG. 10B is a cross-sectional view of the valve holder of FIG. 10A coupled to the valve of FIG. 1.

The inner body 820 is sized to fit within the cylindrical wall 814 of the outer body 810. When the inner body 820 is positioned in the outer body 810, the first guide surface 816 and the second guide surface 826 generally align with one another to form a continuous or nearly continuous guide surface. Prior to implantation of valve 10, the inner body 820 may be assembled in the outer body 810 and advanced over the outflow portion of valve 10, as illustrated in FIG. 10B. As the assembly 810/820 is advanced, the first guide surface 816 of the outer body may contact the commissure posts 30, deflecting them radially inward. As advancement continues further, the second guide surface 826 of the inner body 820 may also contact the commissure posts 30, deflecting them radially inward even farther.

Figure 10C:
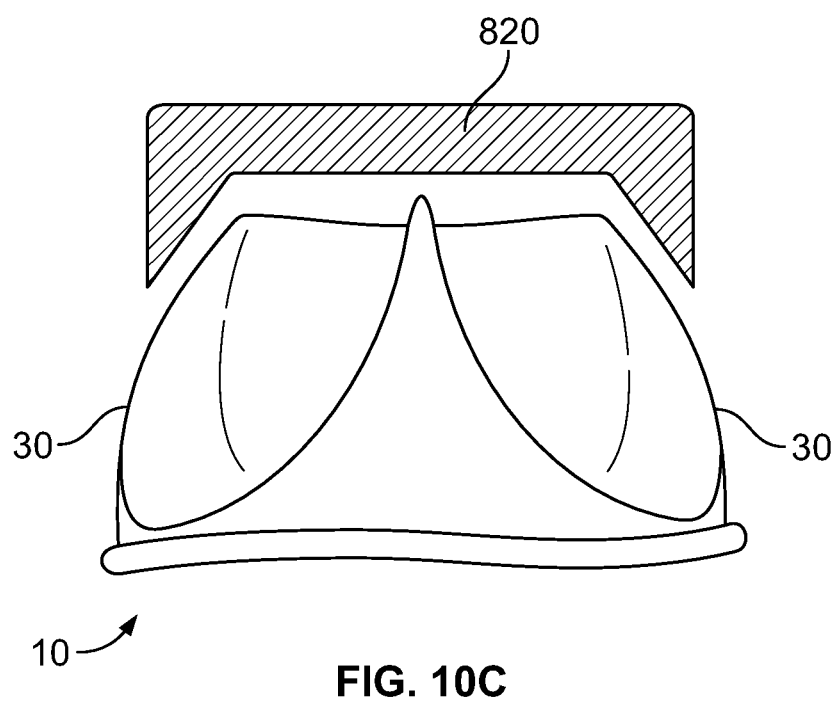
FIG. 10C is a cross-sectional view of the valve holder of FIG. 10A after a component thereof has been removed from the valve.

After the assembly 810/820 has been advanced fully into valve 10, the outer body 810 may be removed, leaving the inner body 820 in place, as illustrated in FIG. 10C. In this configuration, the commissure posts 30 remain constricted, but the effective diameter of the valve holder 800 is reduced by removal of the larger outer body 810. Although not illustrated, the inner body 820 and/or the outer body 810 may include an aperture for connecting a handle to the holder 800 in a manner similar to those described above in connection with the other embodiments of the valve holder. Similarly, although the valve holder 800 has been described as including outer and inner bodies with circular top portions 812, 822 and cylindrical walls 814, 824, the bodies need not have fully circular top portions or fully cylindrical walls. For example, only the portions of the walls configured to make contact with the commissure posts 30 need to provide a guide surface for constricting the valve 10. For a valve 10 with three leaflets 20 and three commissure posts 30, the holder 800 may have a tri-lobe shape with walls extending from the tri-lobe shape in three discrete locations corresponding to the locations of the commissure posts. Similarly, more than two bodies may be provided, with the ultimate goal of minimizing the size of the innermost body that remains in place while still enabling that body to provide sufficient support to the commissure posts 30 to keep them in a constricted configuration.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. Further components of certain embodiments disclosed herein may be combined with other described embodiments without departing from the scope of the invention.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic valve implantation system comprising:
   a prosthetic valve including a stent having a plurality of commissure posts, and a valve assembly mounted within the stent; and
   a holder adapted for connection to the prosthetic valve in an assembled condition, the holder including:
   a base having an axis extending in an axial direction;
   a plurality of legs each extending in a direction from a first end connected to the base toward a free end, the direction including a component in the axial direction;
   a plurality of arcuate fingers each having a concave surface, a convex surface, a first end pivotably coupled to a corresponding one of the plurality of legs, and a free end, each finger having a first position in which the free end is spaced from the axis of the base a first distance and a second position in which the free end is spaced from the axis of the base a second distance less than the first distance, wherein the concave surface is adapted to contact one of the plurality of commissure posts as the finger transitions from the first position to the second position when the holder is in the assembled condition; and
   a suture extending along the convex surface of the finger and having a relaxed state and a tensioned state, wherein the suture transitioning from the relaxed state to the tensioned state is configured to cause the finger to transition from the first position to the second position.

2. The system of claim 1, wherein the convex surface of each one of the fingers includes an arcuate groove extending along the convex surface and at least one suture retaining element extending across the groove.

3. The system of claim 2, wherein the suture extends between the groove and the at least one suture retaining element of each one of the fingers.

4. The system of claim 3, wherein in the assembled condition each one of the fingers is positioned radially outward of a respective one of the commissure posts and the plurality of commissure posts define a circle having an unconstricted diameter in the relaxed state of the suture, and each one of the fingers is positioned radially outward of a respective one of the commissure posts and the plurality of commissure posts define a circle having a constricted diameter in the tensioned state of the suture, the constricted diameter being smaller than the unconstricted diameter.

\* \* \* \* \*